(12) United States Patent
Walls et al.

(10) Patent No.: US 10,669,844 B2
(45) Date of Patent: Jun. 2, 2020

(54) CHARACTERIZING A WELLBORE DEPTH INTERVAL FROM ROCK FRAGMENTS

(71) Applicant: Ingrain, Inc., Houston, TX (US)

(72) Inventors: Joel Walls, Houston, TX (US); Bryan Guzman, Houston, TX (US); Michael Foster, Houston, TX (US); Jonas Toelke, Houston, TX (US); Venkata Ajay Gundepalli, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 174 days.

(21) Appl. No.: 14/904,392

(22) PCT Filed: Jul. 11, 2014

(86) PCT No.: PCT/US2014/046311
§ 371 (c)(1),
(2) Date: Jan. 11, 2016

(87) PCT Pub. No.: WO2015/006670
PCT Pub. Date: Jan. 15, 2015

(65) Prior Publication Data
US 2016/0146002 A1     May 26, 2016

Related U.S. Application Data

(60) Provisional application No. 61/845,272, filed on Jul. 11, 2013.

(51) Int. Cl.
*E21B 49/00* (2006.01)
*E21B 49/02* (2006.01)
(Continued)

(52) U.S. Cl.
CPC .............. *E21B 49/00* (2013.01); *E21B 49/02* (2013.01); *G01N 21/35* (2013.01); *G01N 21/65* (2013.01);
(Continued)

(58) Field of Classification Search
CPC ....................................................... E21B 49/02
See application file for complete search history.

(56) References Cited

U.S. PATENT DOCUMENTS 8,155,377 B2    4/2012  Dvorkin et al.
2009/0259446 A1* 10/2009  Zhang ..................... E21B 49/00
                                                              703/2

(Continued)

FOREIGN PATENT DOCUMENTS

| CN | 101082277 | 12/2007 |
| EA | 013377 B1 | 4/2010 |
| WO | 2015/006670 | 1/2015 |

OTHER PUBLICATIONS

"Extended EP Search Report", dated Feb. 17, 2017, Appl No. 14835085.3, "Conditioning of Expanded Porosity," Filed Aug. 8, 2014, 10 pgs.

(Continued)

Primary Examiner — Raj R Gupta
(74) Attorney, Agent, or Firm — Chamberlain Hrdlicka (57) ABSTRACT

Methods and systems for characterizing a wellbore depth interval from rock fragments, including a method that includes converting measurements of a bulk rock fragment sample and of individual rock fragment samples to a concentration percent, computing a normalization deviation for each of the individual rock fragment samples relative to the bulk rock fragment sample (said normalization deviation being derived from the concentration percent of the bulk and individual rock fragment samples) and ranking the individual rock fragment samples based on a corresponding (Continued)

normalization deviation. The method further includes selecting one or more individual rock fragment samples based on a corresponding ranking, characterizing the properties of the wellbore depth interval from which the bulk and individual rock fragment samples originated using measured properties of at least some of the selected individual rock fragment samples and presenting to a user the characterized wellbore depth interval.

18 Claims, 5 Drawing Sheets

(51) Int. Cl.
G01N 33/28 (2006.01)
G01N 21/35 (2014.01)
G01N 21/65 (2006.01)
G01N 21/71 (2006.01)
G01N 23/20 (2018.01)
G01N 23/223 (2006.01)

(52) U.S. Cl.
CPC ............ *G01N 21/718* (2013.01); *G01N 23/20* (2013.01); *G01N 23/223* (2013.01); *G01N 33/2823* (2013.01); *G01N 2021/3595* (2013.01)

(56) References Cited

U.S. PATENT DOCUMENTS

| | | |
|---|---|---|
| 2009/0260883 A1 | 10/2009 | Suarez-Rivera et al. |
| 2009/0288880 A1* | 11/2009 | Wojcik ................. G01N 23/046 175/50 |
| 2012/0061082 A1 | 3/2012 | Jensen |
| 2012/0186828 A1 | 7/2012 | Lively et al. |
| 2012/0281883 A1* | 11/2012 | Hurley ............... G01N 21/6458 382/109 |
| 2013/0046469 A1 | 2/2013 | Herron et al. |
| 2013/0073207 A1 | 3/2013 | Ganz |

OTHER PUBLICATIONS

PCT International Search Report and Written Opinion, dated Jan. 9, 2014, Appl No. PCT/US2013/050476, "Nuclear Magnetic Resonance (NMR) Logging Tool Calibration," filed Jul. 16, 2013, 12 pgs.
Harry D. Rowe et al.; "Mississippian Barnett Formation, Fort Worth Basin, Texas: Bulk Geochemical Inferences and Mo-TOC Constraints on the Severity of Hydrographic Restriction," Chemical Geology 257 (2008) 16-25, Elsevier B.V.

* cited by examiner

CHARACTERIZING A WELLBORE DEPTH INTERVAL FROM ROCK FRAGMENTS

CROSS-REFERENCE TO RELATED APPLICATION

This application claims priority to Provisional U.S. Application Ser. No. 61/845,272, titled "Method for Characterizing a Wellbore Depth Interval from Rock Fragments" and filed Jul. 11, 2013 by Joel Walls, Bryan Guzman, Michael Foster, Jonas Toelke Venkata Ajay Gundepalli, which is incorporated herein by reference.

BACKGROUND

Oilfield operators drill wellbores to access subterranean reservoirs. Often they desire to characterize the formations that are penetrated by the wellbores. For example, such characterization facilitates estimation of the amount and accessibility of hydrocarbons in reservoir rocks. However, it can be difficult to perform such characterization, particularly when it is infeasible to insert appropriate tools in the wellbore and/or to obtain core samples.

It would be desirable to characterize the penetrated formations based on the rock fragments obtained from the drilling process itself. Such a process preferably would overcome certain obstacles, e.g., the fragments are necessarily much smaller than core samples, only statistically associated with given wellbore intervals, and subject to contamination by the drilling fluid used to flush them from the wellbore.

BRIEF DESCRIPTION OF THE DRAWINGS

A better understanding of the various disclosed embodiments can be obtained when the following detailed description is considered in conjunction with the attached drawings, in which.

It should be understood that the drawings and corresponding detailed description do not limit the disclosure, but on the contrary, they provide the foundation for understanding all modifications, equivalents, and alternatives falling within the scope of the appended claims.

DETAILED DESCRIPTION

The paragraphs that follow describe illustrative methods and systems for characterizing a wellbore depth interval from rock fragments. Illustrative drilling environments are first described, followed by a description of the separation of rock fragments produced by drilling operations into at least two samples. The preparation of the rock fragment samples is then described, followed by a description of several methods that process and combine measurements of the samples to produce a characterization of the rock for the depth interval from which the samples originated. The disclosed methods are also presented within the context of an illustrative system and a software-based implementation by said system. Together, the system and software may perform at least part of the disclosed methods to characterize the depth interval of interest.

Figure 1:
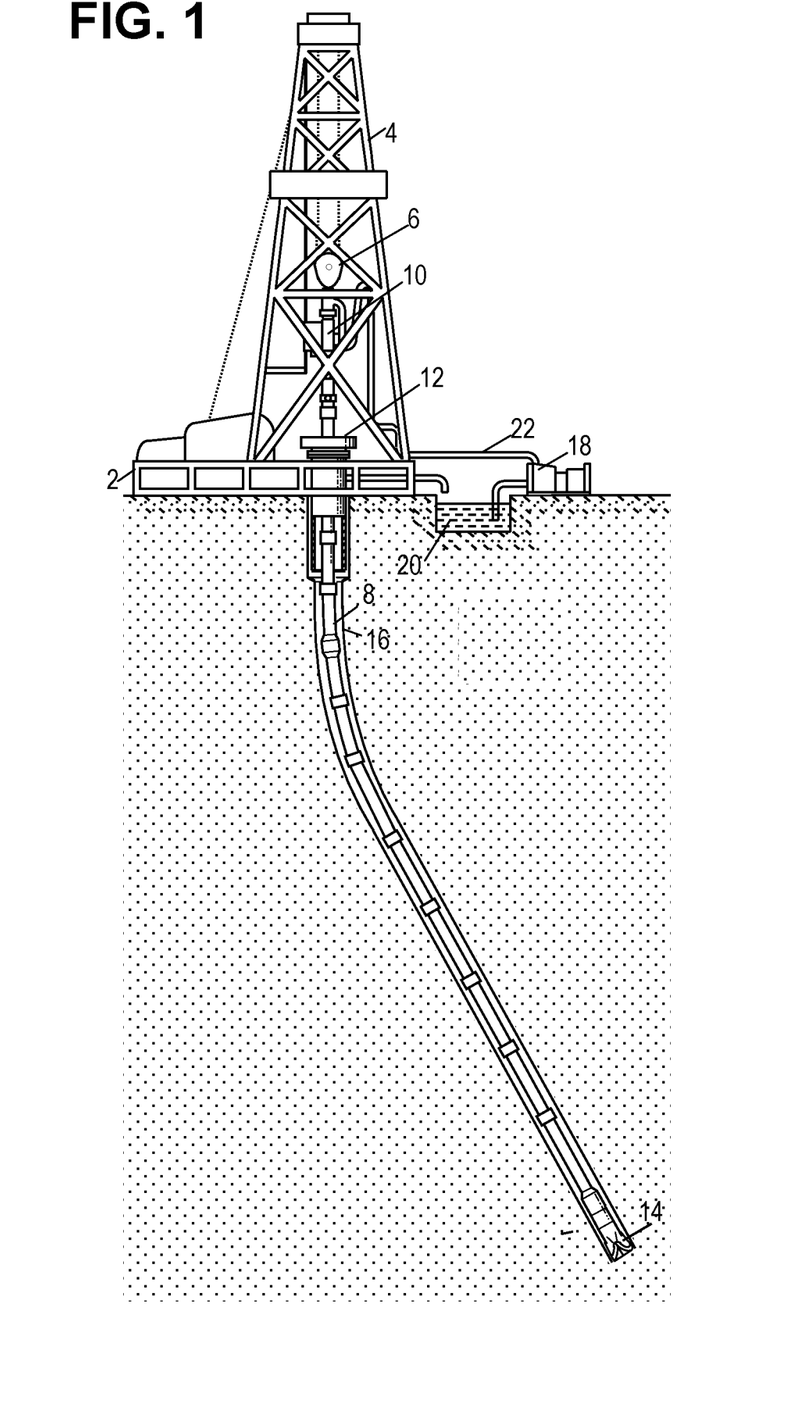
FIG. 1 is a schematic diagram of an illustrative drilling environment.

The disclosed methods and systems are best understood in the context of the larger systems in which they operate. Accordingly, FIG. 1 shows an illustrative drilling environment. A drilling platform 2 supports a derrick 4 having a traveling block 6 for raising and lowering a drill string 8. A top drive 10 supports and rotates the drill string 8 as it is lowered through the wellhead 12. A drill bit 14 is driven by a downhole motor and/or rotation of the drill string 8. As bit 14 rotates, it creates a wellbore 16 that passes through various formation layers. A pump 18 circulates drilling fluid 20 through a feed pipe 22, through the interior of the drill string 8 to drill bit 14. The fluid exits through orifices in the drill bit 14 and flows upward through the annulus around the drill string 8 to transport rock fragments or "cuttings" to the surface. At the surface, the drilling fluid is filtered to remove the rock fragments and the drilling fluid is recirculated back down the drill string 8 to repeat the process.

The rock fragments filtered out from the drilling fluid are representative of the rock formation depth interval from which they originate from. The disclosed methods identify one or more rock fragments that best represent the depth interval of the thousands of rock fragments transported to the surface. The disclosed methods provide a cost-effective way to investigate and characterize a formation that provides a valid representation of the intervals of interest.

Figure 2:
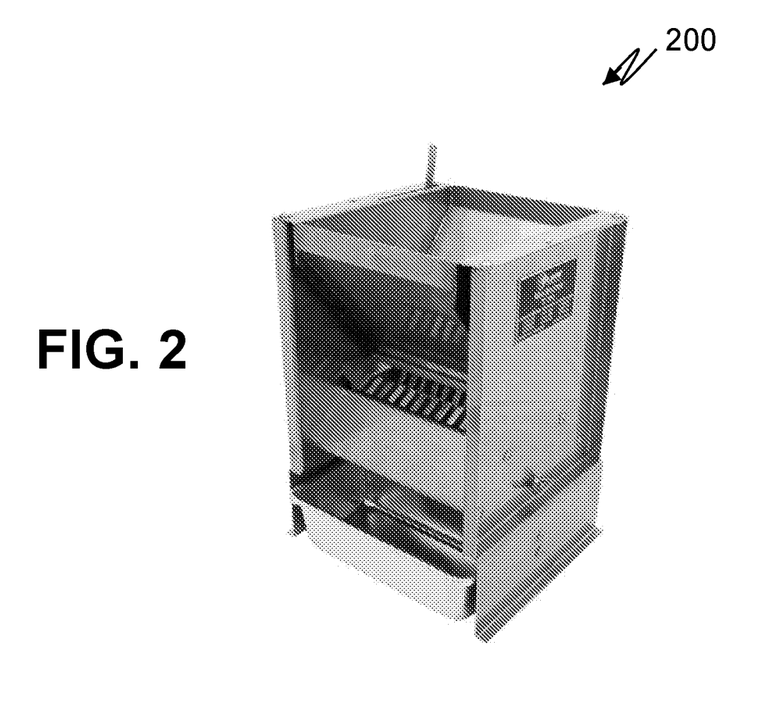
FIG. 2 is an image of an illustrative sample splitter.

In at least some illustrative embodiments, the rock fragments are delivered to a lab still mixed with the drilling fluid, which is removed from the rock fragments so that they can be analyzed more accurately. Once they have been cleaned, the rock fragments from the interval are divided into at least two fractions (e.g., divisions A & B). These fractions are maintained consistent with each other so that the analysis performed on each fraction and the corresponding results are also consistent (since they are from the same depth interval). This consistency is achieved by using a sample splitter for unbiased splitting (e.g. Gilson Universal Stainless Steel Mini-Splitter; many other splitters are known in the art and are not discussed further), such as splitter 200 shown in FIG. 2. In other illustrative embodiments, additional divisions (e.g., division C, division D, etc.) may be produce for additional bulk and individual cuttings analysis performed in addition to the analysis of divisions A & B described below.

Figure 3:
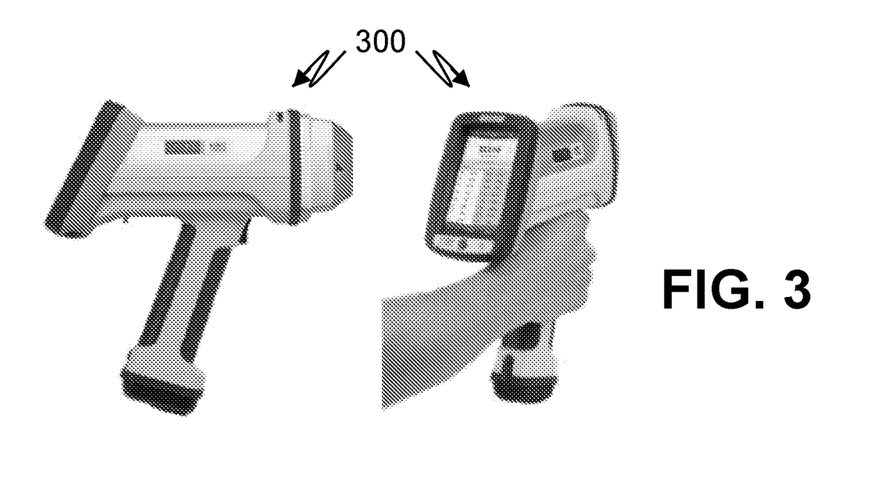
FIG. 3 is an image of an illustrative handheld micro X-ray fluorescence device.

The division A sample is prepared for analysis, for example, for XRF analysis by pulverizing the sample and pressing the resulting powder into a pellet that is analyzed using a handheld micro-XRF device such as XRF device 300 shown in FIG. 3, though other non-handheld devices may also be used. In XRF analysis a sample is exposed to short-wavelength X-rays, ionizing the sample's atoms. This ionization results from the ejection of one or more inner orbital electrons of the atoms. This creates instability in the atom and electrons in higher orbitals drop down into the lower orbitals, releasing energy in the form of a photon. This absorption and subsequent re-emission of radiation in this manner is referred to as fluorescence. The XRF device analyzes the fluorescent radiation by sorting the energies of the photons (energy-dispersive analysis) and/or by separating the wavelengths of the radiation (wavelength-dispersive analysis). The composition of a sample can be determined from this analysis because the intensity of each element's characteristic radiation is directly related to the amount of that element in the sample.

It should be noted that although the examples described herein are presented within the context of XRF measurements and analysis, the disclosed combination of bulk sample analysis and individual cuttings sample analysis is not limited to XRF measurements and analysis. Many other sample measurement and analysis techniques such as X-ray diffraction (XRD), Fourier transform infrared spectroscopy (FTIR), laser-induced breakdown spectroscopy (LIBS), Raman spectroscopy and/or any other type of electromagnetic spectroscopy, are suitable for use within the methods and systems described, and all such measurement and analysis techniques are within the scope of the present disclosure.

For illustrative embodiments utilizing XRF analysis, the division A sample is pulverized and placed into a sample die and then covered with a binding powder (e.g., boric acid, cellulose, etc.). The die is placed under a press that compresses the sample using significant pressure (e.g., 20 tons of pressure), yielding a uniform pellet. In other illustrative embodiments, fused beads or pellets may also or instead be produced. The resulting pellet is analyzed using, for example, XRF 300 of FIG. 3 to determine the sample's elemental composition. The XRF device 300 is pointed at the sample and activated to expose the sample to radiation and measure the resulting re-emissions. The result is displayed on the device as show, and may also be transferred to a computing system for further processing as discussed in more detail below. Results from the elemental analysis of this pellet are now considered representative of the rock composition throughout the sample interval and are referred to as the bulk analysis results.

The division B sample (which is from the same depth interval as the division A sample) is repeatedly subdivided with the sample splitter (a device that provides an unbiased segregation of rock fragments within a sample) until the desired amount of rock fragments remain (e.g., 20-30 rock fragments). The remaining rock fragments are placed on a flat surface and mounted in epoxy. In at least some illustrative embodiments, this mounting is performed under vacuum. The resulting epoxy chip containing the rock fragments is ground down until at least one face of each rock fragment is exposed with rough polish. This enables each rock fragment's surface to be analyzed utilizing XRF techniques. As with the bulk sample, other measurement and analysis techniques, such as those previously described, may be applied to the exposed rock fragment.

After measurements are performed on both division A and division B samples, the measurements are processed and converted into a concentration percent such as weight percent or volume percent. For the illustrative XRF embodiment presented, the XRF counts are processed using an appropriate calibration so that the counts can be converted into elemental weight percent. An example of such a calibration is described in Rowe, Loucks, Ruppel, and Rimmer, "Mississippian Barnett Formation, Ft Worth Basin, Tex.: Bulk Geochemical Inferences and Mo-TOC Constraints on the Severity of Hydrographic Restriction", Chemical Geology 257 (2008) 16-25. Certain elements may be emphasized more than others based on expected formation properties. After both the bulk analysis sample (division A) and the individual rock fragment sample (division B) are converted into elemental weight percent, the individual rock fragment sample (division B) can be compared to the bulk analysis sample (division A). In at least some illustrative embodiments, a normalized deviation of the elemental weight percent of the division B samples vs. the bulk elemental weight percent (see examples below) is computed by selecting a base element using descriptive statistics based on weight percentage from the bulk analysis. The individual rock fragments are ranked based on this normalized deviation, and one or more of these rock fragments are selected based on their ranking.

Once ranked, the selected rock fragments are imaged using any one of numerous techniques, including but not limited to white light, X-ray projection and X-Ray computerized tomography. In at least some illustrative embodiments, the resulting images, along with the sample rankings, are used to select the final rock fragments measured to determine rock properties such as, e.g., porosity, absolute and relative permeability, elasticity, electrical properties, etc. Such properties may be evaluated based on the normalized deviation, with a smaller deviation rock fragment considered representative of the typical rock properties for the interval and the larger deviation rock fragments defining the range of rock properties for the interval.

Figure 4:
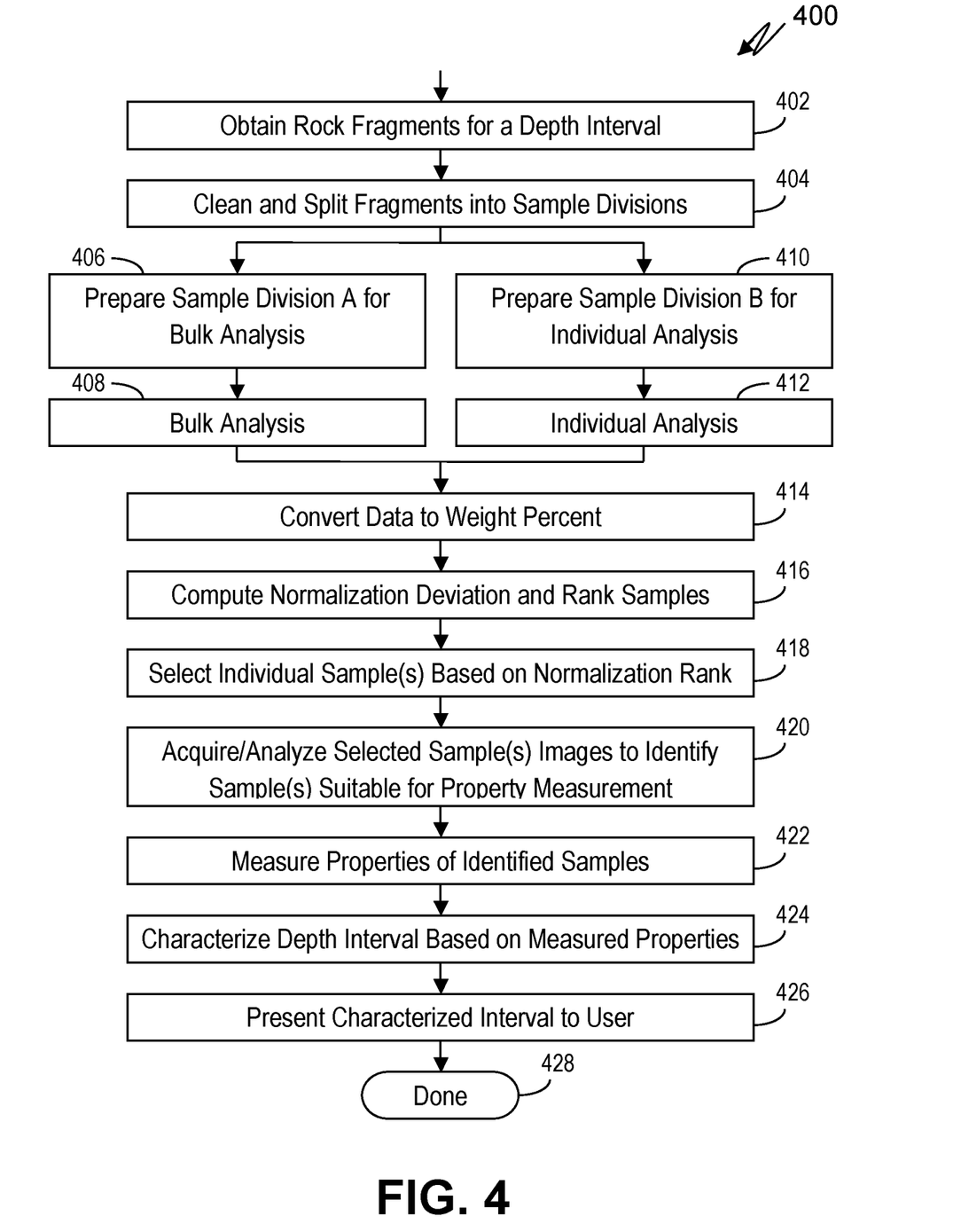
FIG. 4 is a flowchart showing an illustrative method for characterizing a wellbore depth interval from rock fragments.
Figure 5:
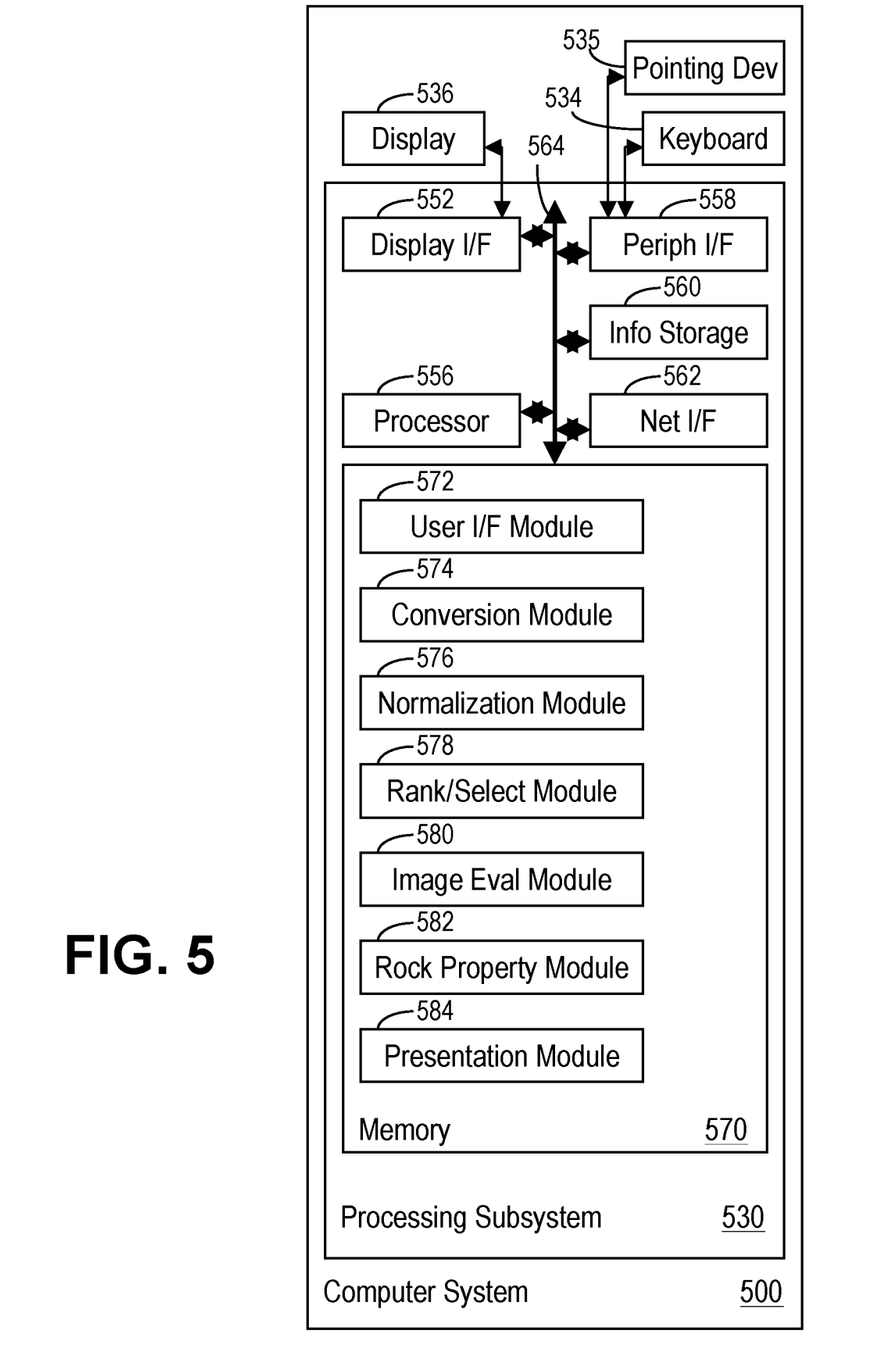
FIG. 5 is a block diagram of a computer system suitable for implementing at least part of the disclosed methods in software.

FIG. 4 shows an illustrative flowchart for the above-described method, while FIG. 5 shows a block diagram of a computer system 5. Both hardware and software components of computer system 500 are shown, which in at least some illustrative embodiments implement at least part of the wellbore depth interval characterization shown as method 400 in FIG. 4 (described in detail below). A user may interact with computer system 500 via keyboard 534, pointing device 535 (e.g., a mouse) and display 536 to configure, control and monitor the execution of the wellbore depth interval characterization.

Located within processing subsystem 530 of computer system 500 is a display interface 552, a processor 556, a peripheral interface 558, an information storage device 560, a network interface 562 and a memory 570. Bus 564 couples each of these elements to each other and transports their communications. Network interface 562 enables communications with other systems (e.g., via the Internet with a central database server housing well logging data). In accordance with user input received via peripheral interface 558 and program instructions from memory 570 and/or information storage device 560, processor 556 processes input from the user and applies it to the well logging data to perform the disclosed methods and present the results to the user. Storage device 560 may be implemented using any number of known non-transitory information storage media, including but not limited to magnetic disks, solid-state storage devices and optical storage disks.

Various software modules are shown loaded into memory 570 of FIG. 5, where they are each accessed by processor 556 for execution. These modules include: User Interface Module 572, which interacts with the input/output devices utilized by the user to interact with processing system 530; analysis module 574, which calibrates and analyzes the data for both bulk samples (division A) and individual rock fragment samples (division B); normalization module 576, which performs the normalization computations; ranking and selection module 578, which ranks and selects individual rock fragment samples based on normalization values; image evaluation module 580, which evaluates images of selected individual rock fragment samples; rock property module 582, which determines representative rock properties and a range of rock properties based on selected individual rock fragment samples; and presentations module 584, which present to a user the results of method 500. In at least some illustrative embodiments, the results are presented in graphical form (e.g., as an image of the various bed layers of a formation within a wellbore depth range).

Referring now to both FIGS. 4 and 5, method 400 begins by obtaining rock fragments for a given depth interval from the drilling fluid expelled during drilling of a wellbore (block 402). The drilling fluid is removed from the rock fragments, which are then split into two, unbiased sample divisions (block 404) using a sample splitter as previously described (e.g., 5 grams of division A and 5 grams of division B). The sample for division A is pulverized and formed into a pellet to prepare it for bulk analysis (block 406), and a bulk analysis is performed on the pressed pellet (block 408). Similarly, a sample splitter is repeatedly used to produce an unbiased reduction of the number of individual rock fragments in the sample for division B until the desired number of rock fragments is achieved (e.g., 20-30 rock fragments), with the resulting rock fragments being encased in epoxy to form a wafer with exposed rock fragment faces as previously described (block 410). An individual analysis similar to that performed on the pressed pellet is then performed on each of the rock fragments within the epoxy wafer (block 412).

It at least some illustrative embodiments, the analysis data collected in blocks 408 and 412 is processed by a computer system such as computer system 500 of FIG. 5. The bulk and individual data is converted into concentration percent, e.g., a weight percent using a calibration technique as previously described (block 414; Conversion Module 574). The resulting weight percent values are subsequently used to compute for each individual rock fragment within sample division B a normalized deviation of weight percent versus the bulk weight percent of sample division A (block 416; Normalization Module 576). The following equations are examples of normalized deviations that in at least some illustrative embodiments are based on elemental weight percent:

$$\text{Norm} = \frac{\sum_{i=1}^{N} |W_i - W_{ib}|}{\sum_{i=1}^{N} |W_{ib}|} \quad (1)$$

$$\text{Norm} = \sum_{i=1}^{N} \frac{|W_i - W_{ib}|}{W_{ib}} \quad (2)$$

$$\text{Norm} = \sum_{i=1}^{N} \left| \frac{W_{ib}}{W_Y} - \frac{W_i}{W_X} \right| \quad (3)$$

where
- N=a number of elements or minerals under consideration,
- $W_i$=an individual rock fragment sample's weight percent for element or mineral i,
- $W_{ib}$=the bulk rock fragment sample's weight percent for the element or mineral i,
- $W_Y$=a weight percent of the highest weighted element or mineral in the bulk rock fragment sample, and
- $W_X$=a weight percent of an individual rock fragment sample of the plurality of individual rock fragment samples that corresponding to the highest element or mineral weight percent in the bulk rock fragment sample.

For equation (3), $W_Y$ represents the weight percent of the highest weighted element of the bulk rock fragment sample, which is constant for the corresponding depth interval from which the sample originated. $W_X$ represents the weight percent of the same element, but for the individual rock fragment sample, and this weight percent also remains constant for the depth interval from which the sample originated. Although equations (1)-(3) are expressed in terms of elemental weight percent, in other illustrative embodiments the equations may be based on other types of weight percent such as, for example, mineralogical weight percent or total organic carbon (TOC), just to name two examples, as well as other concentration percentages such as volume percent. Other types of data suitable for use with these equations will become apparent to those of ordinary skill in the art, and all such types of data are within the scope of the present disclosure.

The computed normalized deviations provide a basis for ranking the rock fragments within sample division B (block 416; Rank/Select Module 578) and selecting one or more of the rock fragments based on the rankings (block 418; Rank/Select Module 578). For example, in at least some illustrative embodiments one or more of the rock fragments with the smallest normalized deviations (relative to the bulk sample division) are selected as representative of the rock present in the wellbore depth interval from which the rock fragments originated during drilling.

The selected rock fragments are subsequently imaged using any of a number of imaging techniques (e.g. white light, X-ray projection, X-ray computerized tomography, etc.) so as to ascertain the suitability of the rock fragments for measuring various properties of the rock (block 420; Image Evaluation Module 580). Examples of such properties include, but are not limited to porosity, absolute and relative permeability, elasticity and electrical properties. The suitability of the selected rock fragments may be ascertained based upon, for example, the number of fractures observed, as well as the size and color of the sample. Damaged samples with a high number of fractures can present issues when imaging such samples with a scanning electron microscope (SEM). Also, the size/aspect ratio of a sample can have an effect on sample preparation, and as a result larger samples are preferred. When imaging using white light, color may also be used to identify statistical outliers, thus providing additional criteria for determining the suitability of the selected rock fragments for measuring the properties of interest.

Figure 6:
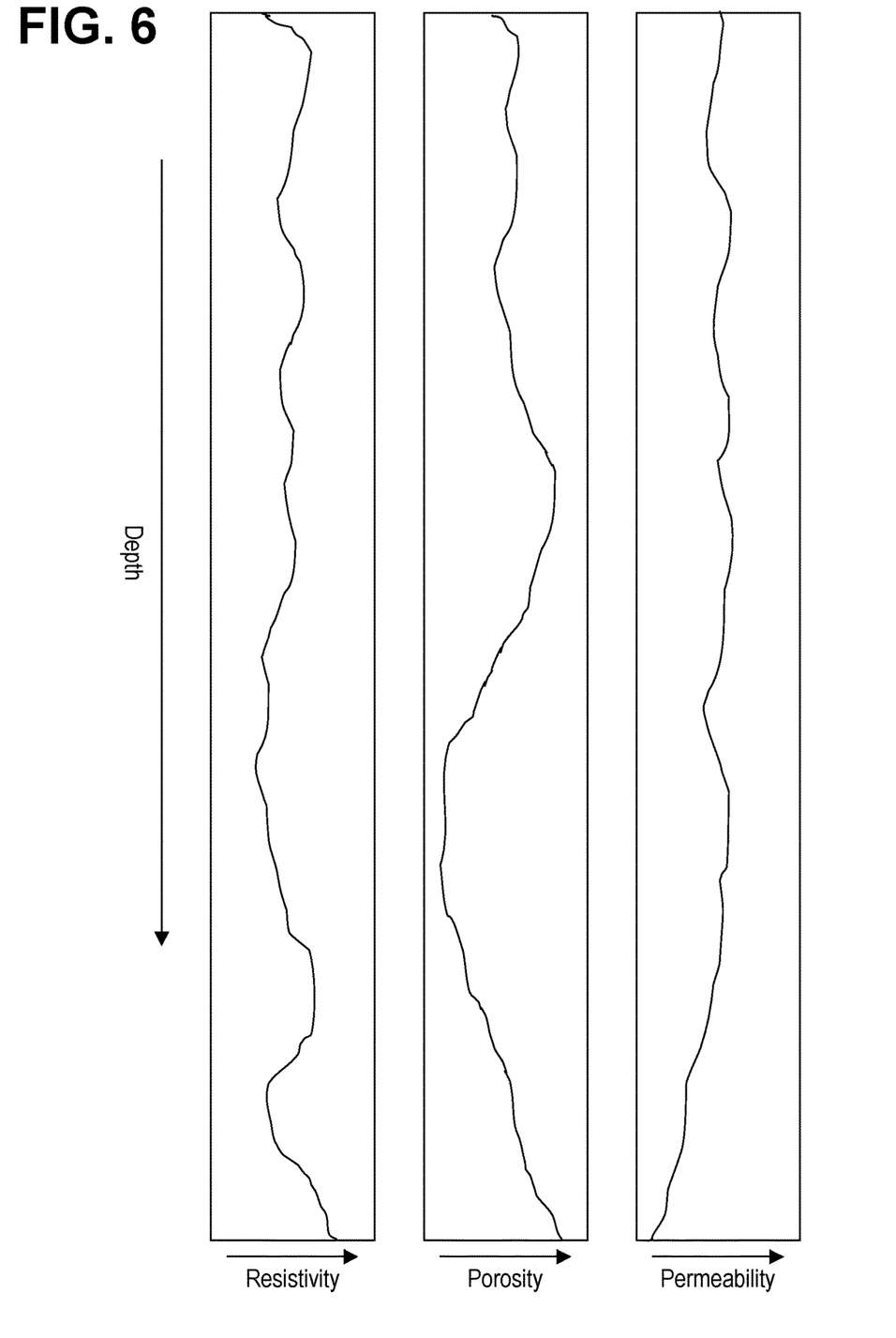
FIG. 6 shows an example of several illustrative well logs of properties of the wellbore.

Rock fragments identified as suitable are selected and their properties measured (block 422; Rock Property Module 582). The properties of the suitable rock fragment with the smallest normalized deviation are treated as representative of the rock properties of the depth interval from which the rock fragment originated, and the properties of suitable rock fragments with larger normalized deviations are used to characterize the range of rock properties with said depth interval (block 424; Rock Property Module 582). The resulting properties are presented to a user of the system (block 426; Presentation Module 584), for example, by graphically representing the formation bed layering traversed by the wellbore to illustrate the various rock types and/or rock properties on a display or image log, or by presenting a well log of one or more of the properties of the wellbore (e.g., as shown in FIG. 6), ending method 400 (block 428). The method thus enables the properties of a rock formation to be characterized through judicious selection of rock fragments that are identified as being most representative of the depth interval from which they originate, allowing the analysis of the samples to be scaled up and applied to the entire interval with a high degree of confidence.

The disclosed methods and systems provides data describing the properties of formation rock that can be used to assist with validation of the target zone for a pilot well and, for horizontal wells, to confirm containment within a target zone before making completion decisions. The disclosed methods and systems can provide such information for wells where LWD or wireline data is not available, and can provide additional data points for determining reserve estimations (e.g., when utilizing SEM data).

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A method for characterizing a wellbore depth interval from rock fragments obtained during drilling of a wellbore, the method comprising:
preparing some of the rock fragments into a bulk rock fragment sample for bulk analysis;
measuring properties of the bull rock fragment sample;
measuring properties of other individual rock fragment samples not part of the bulk rock fragment;
converting, with one or more processors, measurements of the bulk rock fragment sample and of the plurality of individual rock fragment samples to a concentration percent;
computing, with the one or more processors, a normalized deviation for each of the plurality of individual rock fragment samples relative to the bulk rock fragment sample, said normalized deviation being derived from the concentration percent of the bulk and individual rock fragment samples;
ranking, with the one or more processors, the plurality of individual rock fragment samples based on a corresponding normalized deviation;
selecting, with the one or more processors, one or more individual rock fragment samples of the plurality of individual rock fragment samples based on a corresponding ranking;
characterizing, with the one or more processors, the properties of the wellbore depth interval using the measured properties of at least some of the selected one or more individual rock fragment samples; and
displaying the characterized wellbore depth interval.

2. The method of claim 1, further comprising identifying the at least some of the one or more individual rock fragment samples by imaging, with a device, each of the one or more individual rock fragment samples and analyzing the resulting images.

3. The method of claim 2, wherein the imaging is performed using an imaging technique selected from the group consisting of white light imaging, X-ray projection imaging and X-ray computerized tomography imaging.

4. The method of claim 1, further comprising:
cleaning the rock fragments and splitting the cleaned rock fragments into at least two unbiased sample divisions, a first division of the two unbiased sample divisions comprising the bulk rock fragment sample and a second division of the two unbiased sample divisions comprising the plurality of individual rock fragment samples;
pulverizing the rock fragments of the bulk rock fragment sample and compressing the pulverized rock fragments into a pellet;
encasing the plurality of individual rock fragment samples in epoxy to form a wafer and removing some of the epoxy and exposing a portion of each of the plurality of individual rock fragment samples; and
acquiring the measurements of the pellet and of the exposed portion of each of the plurality of individual rock fragment samples.

5. The method of claim 1, wherein the normalized deviation is computed using an equation selected from the group consisting of $$\frac{\sum_{i=1}^{N} |W_i - W_{ib}|}{\sum_{i=1}^{N} |W_{ib}|},$$

$$\sum_{i=1}^{N} \frac{|W_i - W_{ib}|}{W_{ib}}, \text{ and}$$

$$\sum_{i=1}^{N} \left| \frac{W_{ib}}{W_Y} - \frac{W_i}{W_X} \right|,$$

where,
N=a number of elements or minerals under consideration,
$W_i$=an individual rock fragment sample's weight percent for element or mineral i,
$W_{ib}$=the bulk rock fragment sample's weight percent for the element or mineral i,
$W_Y$=a weight percent of the highest weighted element or mineral in the bulk rock fragment sample, and
$W_X$=a weight percent of an individual rock fragment sample of the plurality of individual rock fragment samples that corresponding to the highest element or mineral weight percent in the bulk rock fragment sample.

6. The method of claim 1, wherein the characterized wellbore depth interval is presented to a user as part of a graphical representation of formation bed layers traversed by the wellbore or as part of a well log of one or more of the properties of the wellbore.

7. The method of claim 1, wherein the measurements performed are selected from a group of measurement techniques consisting X-ray florescence (XRF), X-ray diffraction (XRD), Fourier transform infrared spectroscopy (FTIR), laser-induced breakdown spectroscopy (LIBS), Raman spectroscopy and electromagnetic spectroscopy.

8. The method of claim 1, wherein the concentration percent comprises a weight percent that comprises an elemental weight percent, a mineralogical weight percent or total organic carbon (TOC).

9. The method of claim 1, wherein the concentration percent comprises a volume percent.

10. The method of claim 1, comprising drilling a wellbore at the wellbore depth interval.

11. A wellbore depth interval characterization system, comprising:
a memory having tubular string centralization software;
one or more processors coupled to the memory, the software causing the one or more processors to:
convert measurements of a bulk rock fragment sample from the wellbore depth interval and of a plurality of individual rock fragment samples from the wellbore depth interval to a concentration percent, wherein the bulk rock fragment sample and the plurality of individual rock fragment samples are obtained during drilling of a wellbore;
compute a normalized deviation for each of the plurality of individual rock fragment samples relative to the bulk rock fragment sample, said normalized deviation being derived from the concentration percent of the bulk and individual rock fragment samples;

rank the plurality of individual rock fragment samples based on a corresponding normalized deviation;

select one or more individual rock fragment samples of the plurality of individual rock fragment samples based on a corresponding ranking; and characterize the properties of the wellbore depth interval from which the bulk and individual rock fragment samples originated using measured properties of at least some of the selected one or more individual rock fragment samples; and a display configured to graphically represent the wellbore depth interval, or present a well log of the wellbore depth interval.

12. The system of claim 11, wherein the software further causes the one or more processors to identify the at least some of the one or more individual rock fragment samples by imaging each of the one or more individual rock fragment samples with a device and analyzing the resulting images.

13. The system of claim 12, wherein the imaging is performed using an imaging technique selected from the group consisting of white light imaging, X-ray projection imaging and X-ray computerized tomography imaging.

14. The system of claim 11, wherein the normalized deviation is computed using an equation selected from the group consisting of $$\frac{\sum_{i=1}^{N} |W_i - W_{ib}|}{\sum_{i=1}^{N} |W_{ib}|},$$

$$\sum_{i=1}^{N} \frac{|W_i - W_{ib}|}{W_{ib}}, \text{ and}$$

$$\sum_{i=1}^{N} \left| \frac{W_{ib}}{W_Y} - \frac{W_i}{W_X} \right|,$$

where,

N = a number of elements or minerals under consideration, $W_i$ = an individual rock fragment sample's weight percent for element or mineral i, $W_{ib}$ = the bulk rock fragment sample's weight percent for the element or mineral i, $W_Y$ = a weight percent of the highest weighted element or mineral in the bulk rock fragment sample, and $W_X$ = a weight percent of an individual rock fragment sample of the plurality of individual rock fragment samples that corresponding to the highest element or mineral weight percent in the bulk rock fragment sample.

15. The system of claim 11, wherein the characterized wellbore depth interval is presented to a user as part of a graphical representation of formation bed layers traversed by the wellbore or as part of a well log of one or more of the properties of the wellbore.

16. The system of claim 11, wherein the measurements performed are selected from a group of measurement techniques consisting X-ray florescence (XRF), X-ray diffraction (XRD), Fourier transform infrared spectroscopy (FTIR), laser-induced breakdown spectroscopy (LIBS), Raman spectroscopy and electromagnetic spectroscopy.

17. The system of claim 11, wherein the concentration percent comprises a weight percent that comprises an elemental weight percent, a mineralogical weight percent or total organic carbon (TOC).

18. The system of claim 11, wherein the concentration percent comprises a volume percent.

* * * * *